US012295878B2

(12) United States Patent
Rodrigues et al.

(10) Patent No.: US 12,295,878 B2
(45) Date of Patent: May 13, 2025

(54) MANDIBULAR ADVANCEMENT DEVICE

(71) Applicant: APAC Health & Medical Distributors PTY LTD, Maroochydore (AU)

(72) Inventors: Daniel Rodrigues, Maroochydore (AU); Angus Olsen, Maroochydore (AU)

(73) Assignee: APAC Health & Medical Distributors PTY LTD, Maroochydore (AU)

( * ) Notice: Subject to any disclaimer, the term of this patent is extended or adjusted under 35 U.S.C. 154(b) by 0 days.

(21) Appl. No.: 17/496,688

(22) Filed: Oct. 7, 2021

(65) Prior Publication Data

US 2022/0110782 A1 Apr. 14, 2022

(51) Int. Cl.
*A61F 5/56* (2006.01)
(52) U.S. Cl.
CPC .................................. *A61F 5/566* (2013.01)
(58) Field of Classification Search
CPC ...... A61F 5/56; A61F 5/566; A61F 2005/563; Y10S 602/902; A61C 7/36; A61C 7/08; A61B 1/24; A63B 71/08; A63B 71/081; A63B 71/085; A63B 2071/086; A63B 2071/088

USPC ................................ 128/848, 859, 861, 862
See application file for complete search history.

(56) References Cited

U.S. PATENT DOCUMENTS

| 10,383,761 B2 * | 8/2019 | Fallon ..................... A61F 5/566 |
| 11,129,745 B2 * | 9/2021 | Remmers ................ A61F 5/566 |
| 2012/0145166 A1 * | 6/2012 | Fallon ..................... A61F 5/566 |
| | | 128/848 |
| 2023/0031988 A1 * | 2/2023 | Purvis .................. A63B 71/085 |

* cited by examiner

*Primary Examiner* — Michelle J Lee
*Assistant Examiner* — Robin Han
(74) *Attorney, Agent, or Firm* — Holzer Patel Drennan (57) ABSTRACT

A mandibular advancement device is provided comprising: an upper tray assembly comprising a rigid upper chassis and a maxillary tray; and a lower tray assembly comprising a rigid lower chassis and a mandibular tray. The upper and lower chassis define an interlocking arrangement configured to releasably lock the upper and lower tray assemblies into a selected one of a plurality of predefined positions. Each of the predefined positions defining a different offset between the upper and lower tray assemblies to enable adjustment of the degree of mandibular advancement when used.

15 Claims, 8 Drawing Sheets

MANDIBULAR ADVANCEMENT DEVICE

CROSS-REFERENCE TO RELATED APPLICATIONS

The present application claims priority under 35 U.S.C. § 119 to Australian Patent Application No. AU2020256297 filed on 12 Oct. 2020 entitled "MANDIBULAR REPOSITIONING DEVICE," the entirety of which is incorporated by reference herein.

TECHNICAL FIELD

The present invention relates to medical devices, and in particular, to mandibular advancement devices.

BACKGROUND ART

Snoring is a common condition that is believed to affect about 40% of adult men and 30% of adult women in Australia. Snoring is caused by a partially closed upper airway (the nose and throat). In particular, collapsed or relaxed neck muscles cause narrowing of the airway thereby restricting airflow in the airway. This in turn causes the surrounding tissue to vibrate causing the snoring sound.

Snoring may be problematic for many reasons, including sleep disruption to the snorer and to others. As such, several devices exist that attempt to prevent snoring, including mandibular advancement devices. These devices advance and hold the lower jaw in a slightly forward position so that the airway is opened to thereby reduce or prevent snoring.

One problem with such mandibular advancement devices of the prior art is that they are often complex. As a result, fitment and adjustment is often performed by a dentist or other suitably qualified professional, and many are designed to be professionally fitted. As a result, these devices are also expensive.

Certain mandibular advancement devices exist which are able to be adjusted by end users, but these devices are generally particularly complex, with many parts which are either adjusted using screws or simply replaced to fit the user. In addition to being complex to use, these devices are often also uncomfortable.

Another problem with mandibular advancement devices of the prior art is that they are difficult to clean. This is particularly problematic in that the devices are used in the mouth for long periods of time (typically overnight), and cleaning of these devices is important.

As such, there is clearly a need for improved mandibular advancement devices.

It will be clearly understood that, if a prior art publication is referred to herein, this reference does not constitute an admission that the publication forms part of the common general knowledge in the art in Australia or in any other country.

SUMMARY OF INVENTION

The present invention is directed to mandibular advancement devices which may at least partially overcome at least one of the abovementioned disadvantages or provide the consumer with a useful or commercial choice.

With the foregoing in view, the present invention in one form, resides broadly in a mandibular advancement device comprising:

an upper tray assembly comprising a rigid upper chassis and a maxillary tray;

a lower tray assembly comprising a rigid lower chassis and a mandibular tray;

wherein the upper and lower chassis define an interlocking arrangement configured to releasably lock the upper and lower tray assemblies into a selected one of a plurality of predefined positions, each of the predefined positions defining a different offset between the upper and lower tray assemblies to enable adjustment of the degree of mandibular advancement when used.

Advantageously, the ability to interlock the upper and lower tray assemblies in a plurality of predefined positions with an interlocking arrangement in upper and lower chassis provides a simple way to adjust the mandibular advancement device. It does not require additional parts, such as tabs, screws, rods or arms to provide the mandibular advancement. This in turn simplifies both manufacturing and cleaning of the mandibular advancement device and prevents discomfort from external coupling mechanisms.

Preferably, the different offsets define different levels of anterior protrusion of the lower tray relative to the upper tray. The offsets may be defined by translation of the upper tray assembly relatively to the lower tray assembly. The offsets may be substantially entirely defined along a posterior-anterior axis of the mandibular advancement device.

Preferably, at least about 3 different offsets are provided by the predefined positions. Suitably, about 10 different offsets may be provided.

Preferably, the different offsets include offsets between about 0 and 10 mm.

Preferably, the different offsets are provided at increments of about 1 mm.

Preferably, the mandibular advancement device includes indicia to identify a chosen offset. The indicia may be provided on the upper and/or lower chassis. The indicia may comprise markings.

Preferably, the upper and lower chassis are rigidly connected by the interlocking arrangement in use.

Preferably, the interlocking arrangement includes a locking member and an at least partly corresponding locking recess or aperture, wherein relative translation of the upper and lower chassis is prevented in at least a transverse direction when the locking member is in the locking recess or aperture.

Preferably, the locking member is substantially uniform in cross section.

Preferably, the locking member extends outwardly from one of the upper and lower chassis, and the locking recess or aperture is defined in the other of the upper and lower chassis.

The locking member may engage with the locking recess or aperture along the vertical axis.

The locking member may be keyed to at least part of the locking recess or aperture.

The locking recess or aperture may comprise an elongate locking channel, wherein the locking member is configured to be received in one of a plurality of predefined positions in the locking channel.

The locking channel may include a repeating locking pattern, wherein the predefined positions are defined by the locking pattern.

The locking member may include a pattern along its edges corresponding to a portion of the repeating locking pattern of the locking channel. The pattern may be defined in a cross-sectional profile of the locking member.

The locking member may include a plurality of repeated projections along its sides, to correspond with corresponding recesses in the locking channel. The repeated projections and recesses may be defined by a sawtooth pattern.

The mandibular advancement device may include a locking member and corresponding locking recess or aperture in each of a pair of opposed posterior ends.

Preferably, the interlocking arrangement includes a guide member and a locking channel, wherein separation of the upper and lower chassis is prevented in a vertical direction when the guide member is in the locking channel.

The guide member and the locking channel may engage with each other in a dovetail-like arrangement.

The guide member and locking member may be located at anterior portions of the upper and lower chassis.

The mandibular advancement device may include a guide member and corresponding locking channel in each side of an anterior end of the device.

The interlocking arrangement may comprise a combination of a) a locking member and locking recess or aperture to prevent relative movement in a transverse direction, and b) a guide member and corresponding locking channel to prevent separation in a vertical direction.

Preferably, an opening is defined in an anterior portion of the mandibular advancement device to enable airflow therethrough when used. The opening may be defined by cut-outs in the upper and lower chassis.

Preferably, the mandibular advancement device is substantially U-shaped in plan view. Preferably, the mandibular advancement device is substantially symmetrical. The mandibular advancement device may be symmetrical around the sagittal plane.

Preferably, the maxillary tray conforms to an upper dental arch of a user and the mandibular tray conforms to the lower dental arch of a user.

Preferably, the maxillary tray is formed of another material than the rigid upper chassis. Preferably, the maxillary tray is softer than the rigid upper chassis.

Preferably, the mandibular tray is formed of another material than the rigid lower chassis. Preferably, the mandibular tray is softer than the rigid lower chassis.

Preferably, the rigid upper chassis and the rigid lower chassis are formed of the same material. Preferably, the maxillary tray and the mandibular tray are formed of the same material.

Preferably, the maxillary tray is overmoulded over the rigid upper chassis. Preferably, the mandibular tray is overmoulded over the rigid lower chassis. Such configuration alleviates the need for adhesives or fasteners between the trays and chassis.

Preferably, each of the upper and lower chassis is unitarily formed. Preferably, each of the maxillary tray and mandibular tray is unitarily formed.

Preferably, the maxillary tray and the mandibular tray are formed of thermoplastic, enabling the trays to be heated to form to the user's teeth and gums.

Each of the maxillary tray and mandibular tray include inner and outer walls to engage with buccal and oral surfaces of the teeth.

Any of the features described herein can be combined in any combination with any one or more of the other features described herein within the scope of the invention.

The reference to any prior art in this specification is not, and should not be taken as an acknowledgement or any form of suggestion that the prior art forms part of the common general knowledge.

BRIEF DESCRIPTION OF DRAWINGS

Various embodiments of the invention will be described with reference to the following drawings, in which.

Preferred features, embodiments and variations of the invention may be discerned from the following Detailed Description which provides sufficient information for those skilled in the art to perform the invention. The Detailed Description is not to be regarded as limiting the scope of the preceding Summary of the Invention in any way.

DESCRIPTION OF EMBODIMENTS

Figure 1:
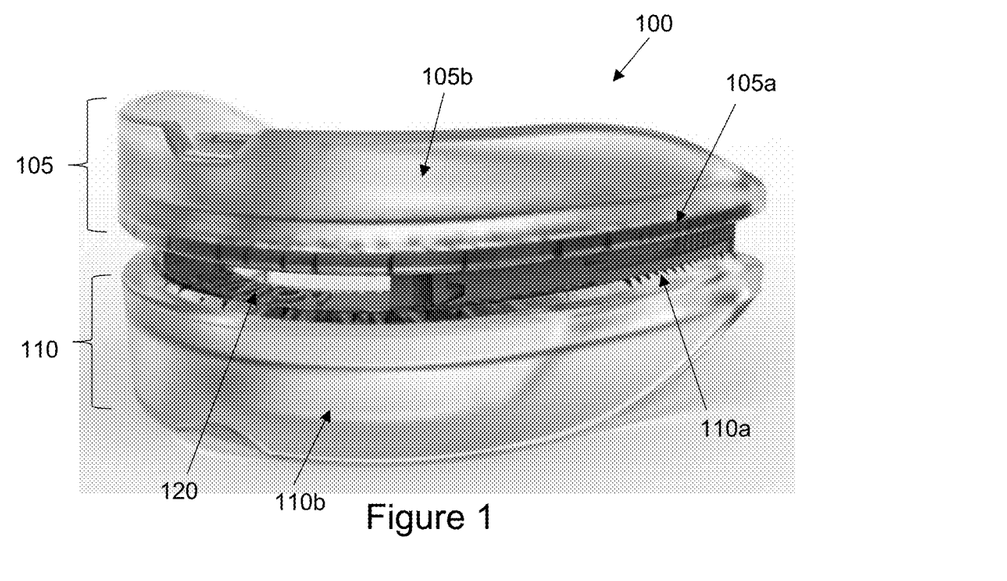
FIG. 1 is a front perspective view of a mandibular advancement device, according to an embodiment of the present invention.

FIG. 1 is a front perspective view of a mandibular advancement device 100, according to an embodiment of the present invention. The mandibular advancement device 100 is configured to be worn by a user during sleep, to hold the mandible (lower jaw) of the user in an advanced position to thereby prevent or reduce snoring.

The mandibular advancement device 100 includes an upper tray assembly 105 comprising a rigid upper chassis 105a and a maxillary (upper) tray 105b, and a lower tray assembly 110 comprising a rigid lower chassis 110a and a mandibular (lower) tray 110b. The maxillary and mandibular trays 105b, 110b are relatively soft and elastomeric and form a U-shaped trough including inner and outer walls that are shaped to conform to the user's and teeth and gums.

The upper and lower chassis 105a, 110a are releasably coupled to each other in a selected one of a plurality of predefined positions, such that the lower tray assembly 110 is adapted to advance the mandible of the user. In particular, each of the predefined positions define a different offset between the upper and lower tray assemblies 105, 110 to enable adjustment of the degree of mandibular advancement when used.

Figure 2:
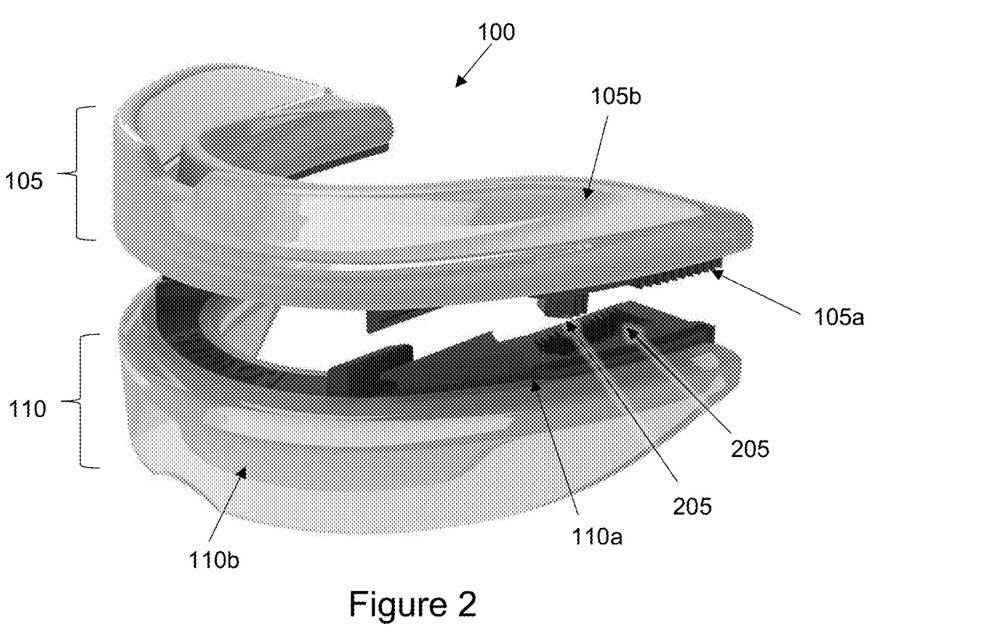
FIG. 2 illustrates an exploded perspective view of the mandibular advancement device of FIG. 1, according to an embodiment of the present invention.

FIG. 2 illustrates an exploded perspective view of the mandibular advancement device 100, according to an embodiment of the present invention. The upper and low chassis 105a, 110a include interlocking arrangement 205 (described in further detail below) and the chassis 105a, 110a are configured to releasably engage with each other to directly and releasable lock the upper and lower chassis 105a, 110a to each other in a rigid manner (i.e. preventing separation and lateral movement). The interlocking arrangement enables the chassis 105a, 110a to be locked in a plurality of predefined positions.

Figure 3:
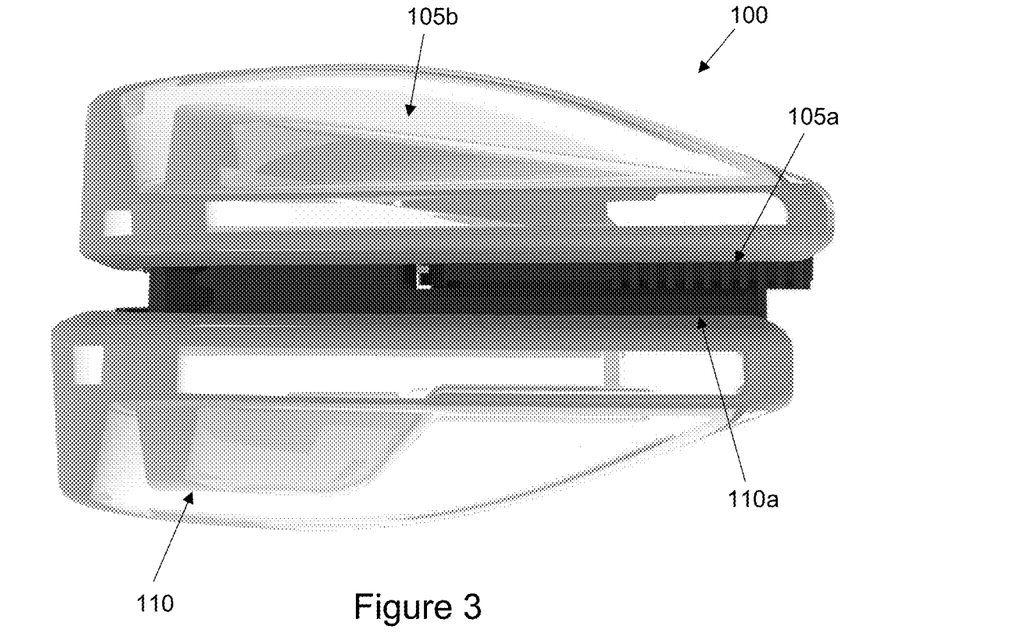
FIG. 3 illustrates a side view of the mandibular advancement device of FIG. 1, in which upper and lower chassis are coupled to each other in a first position thereby providing a first offset between the upper and lower tray assemblies.

FIG. 3 illustrates a side view of the mandibular advancement device 100, in which the upper and lower chassis 105a, 110a are coupled to each other in a first position thereby providing a first offset between the upper and lower tray assemblies 105, 110. In FIG. 3, the offset is relatively small, but the upper and lower tray assemblies 105, 110 may be separated and reattached at different positions to thereby provide an offset that is suitable for the user.

Figure 4:
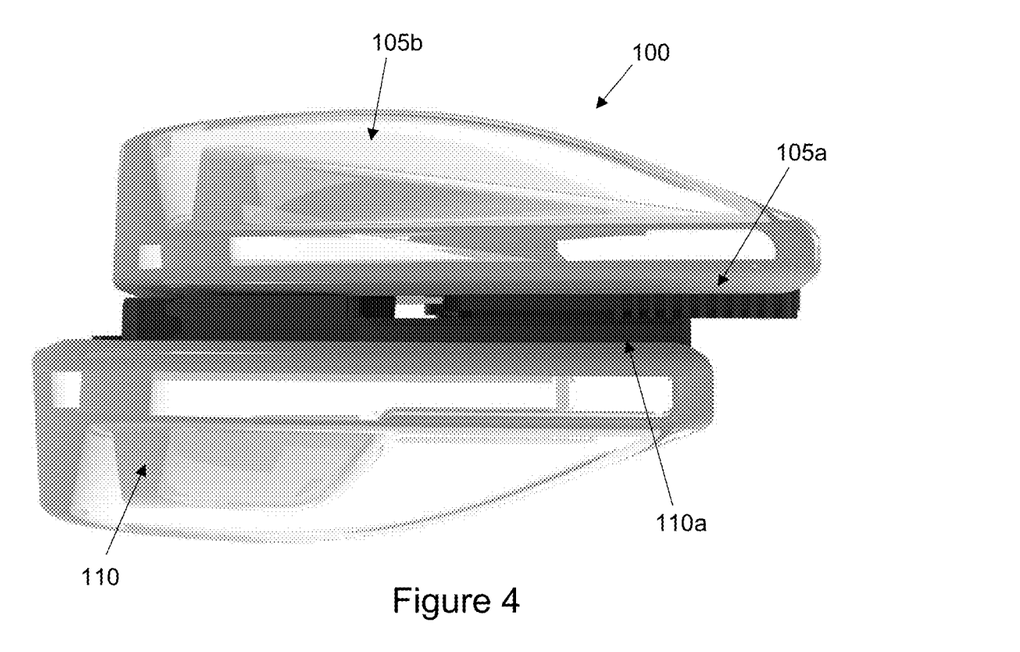
FIG. 4 illustrates a side view of the mandibular advancement device of FIG. 1, in which the upper and lower chassis are coupled to each other in a second position thereby providing a second offset between the upper and lower tray assemblies.

FIG. 4 illustrates a side view of the mandibular advancement device 100, in which the upper and lower chassis 105a, 110a are coupled to each other in a second position thereby providing a second offset between the upper and lower tray assemblies 105, 110. In FIG. 4, the offset is much larger than in FIG. 3, thereby providing further mandibular advancement in such configuration.

Figure 5:
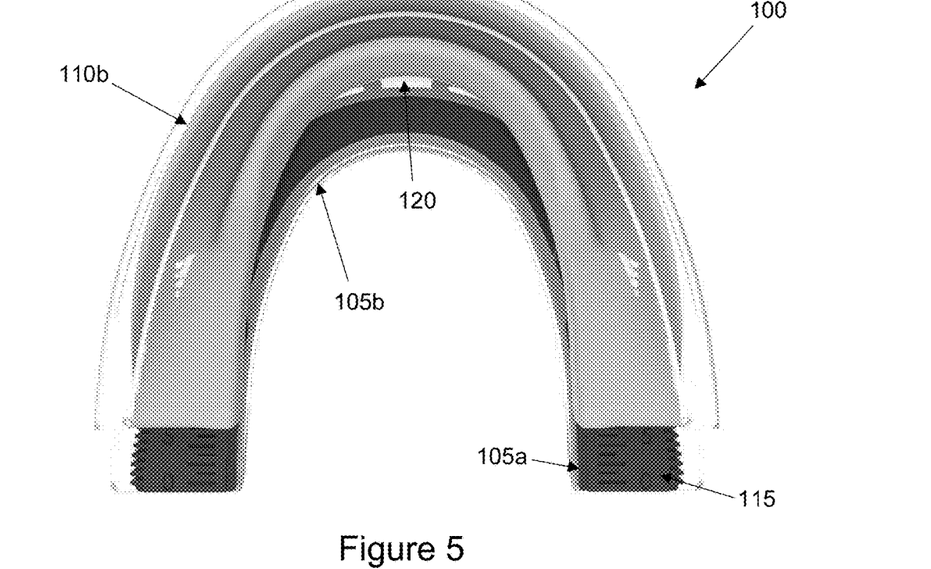
FIG. 5 illustrates a bottom view of the mandibular advancement device of FIG. 1, according to an embodiment of the present invention.

FIG. 5 illustrates a bottom view of the mandibular advancement device 100, according to an embodiment of the present invention.

The mandibular advancement device 100 is substantially U-shaped and substantially symmetrical around the sagittal plane. The upper and lower chassis 105a, 110a and the maxillary and mandibular trays 105b, 110b are similarly substantially U-shaped with a curved anterior portion and a pair of opposed posterior ends. The maxillary tray conforms to an upper dental arch of a user and the mandibular tray conforms to the lower dental arch of a user.

The upper and lower tray assemblies 105, 110, are approximately the same size and shape, and as such, when the lower tray assembly 110 is moved forward relative to the upper tray assembly 105, a rear portion of the upper chassis 105a becomes visible from below. The lower rear portion of the upper chassis 105a is substantially planar, and includes a plurality of measuring indicia 115 to indicate to the user how far offset the upper and lower tray assemblies 105, 110 are, in an easy to read manner.

This, together with the predefined positions, enables a user to try a position, evaluate, and update the position in an easily reproducible manner. As an illustrative example, a user may start at a default setting and gradually increase the offset. If the user finds a setting uncomfortable, he or she is able to revert to the old setting accurately and with ease.

Now turning back to FIG. 1 and FIG. 5, an opening 120 is defined in an anterior portion of the mandibular advancement device 100 between the upper and lower tray assemblies 105, 110. The opening 120 is defined by cut-outs in the upper and lower chassis 105a, 110a as outlined in further detail below. The opening 120 enables air to easily flow in an out of the mouth when the mandibular advancement device 100 is used, thereby enabling mouth breathing while using the mandibular advancement device 100.

Figure 6:
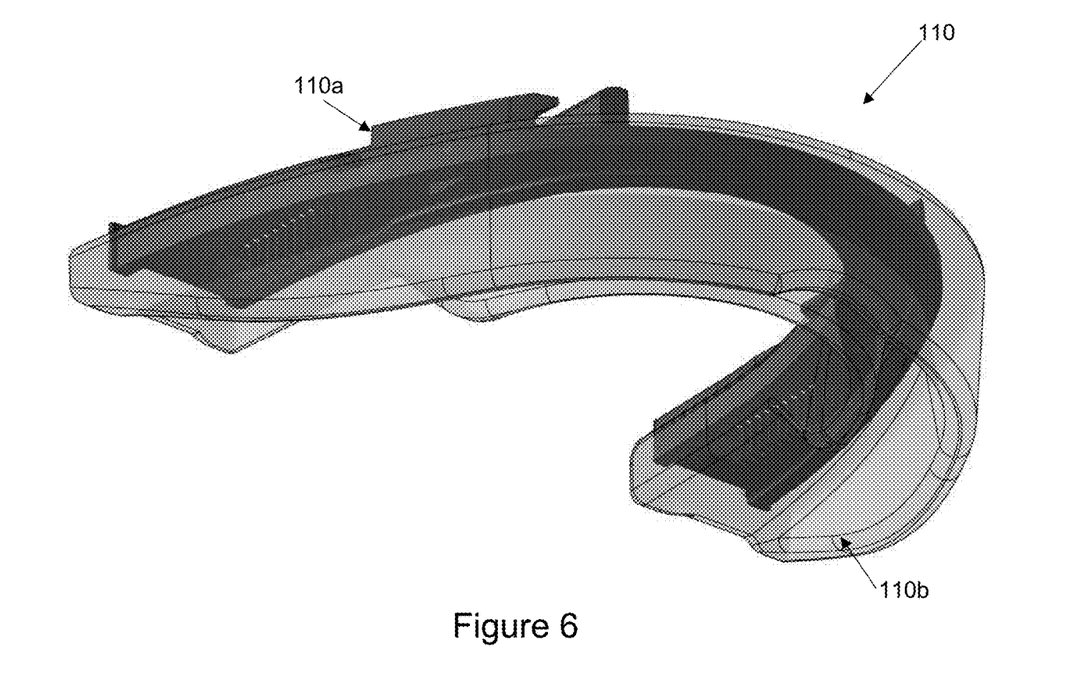
FIG. 6 illustrates a lower perspective view of a lower tray assembly of the device of FIG. 1, according to an embodiment of the present invention.
Figure 7:
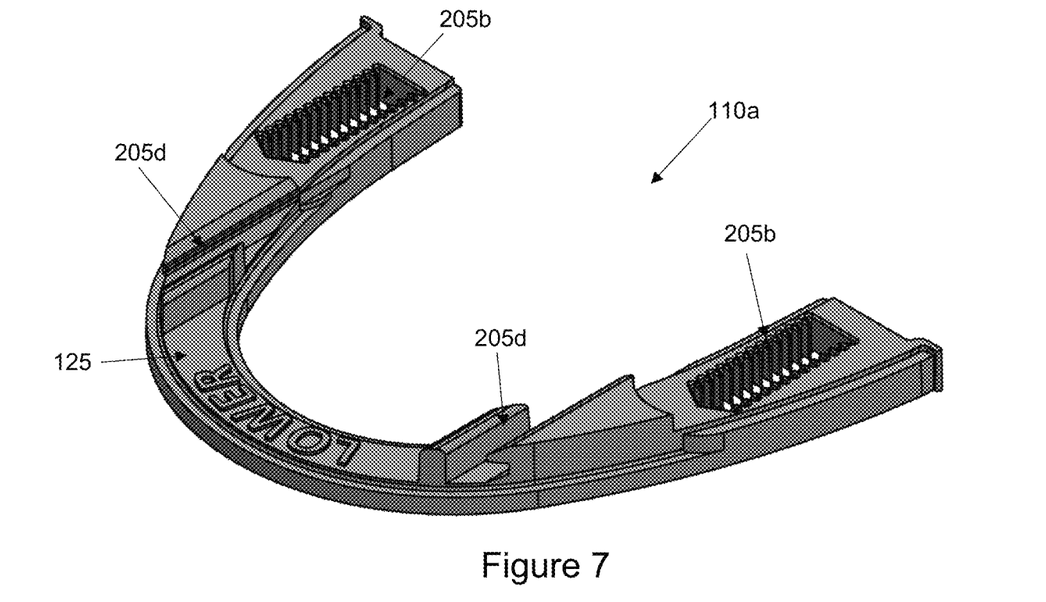
FIG. 7 illustrates an upper perspective view of a lower chassis of the lower tray assembly of FIG. 6.
Figure 8:
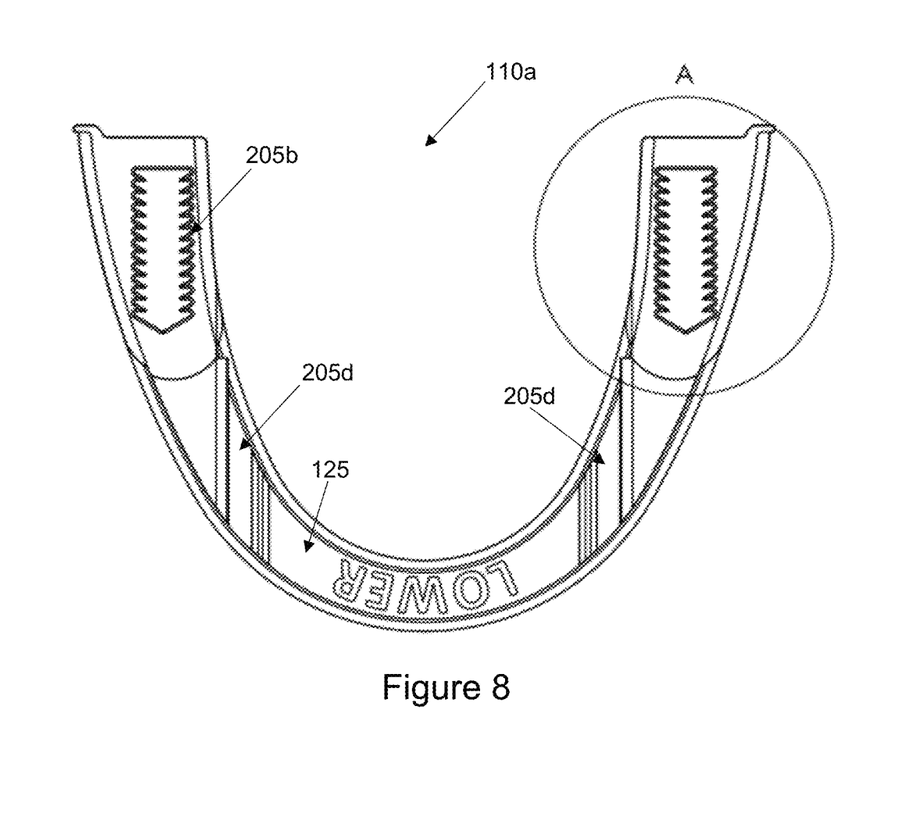
FIG. 8 illustrates a top view of the lower chassis of the lower tray assembly of FIG. 6.
Figure 9:
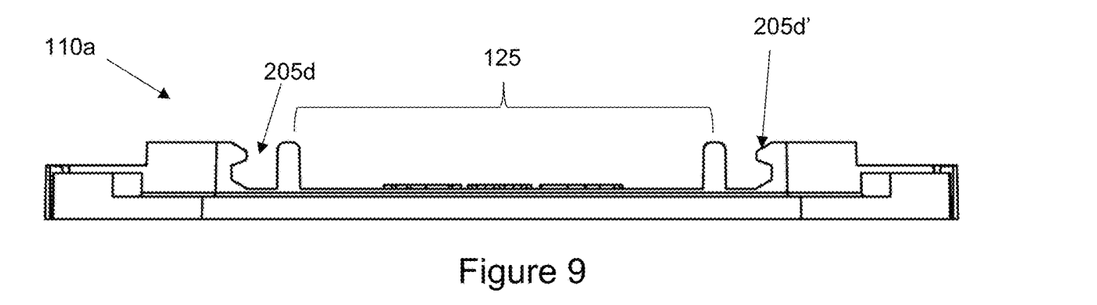
FIG. 9 illustrates an end view of the lower chassis of the lower tray assembly of FIG. 6.
Figure 10:
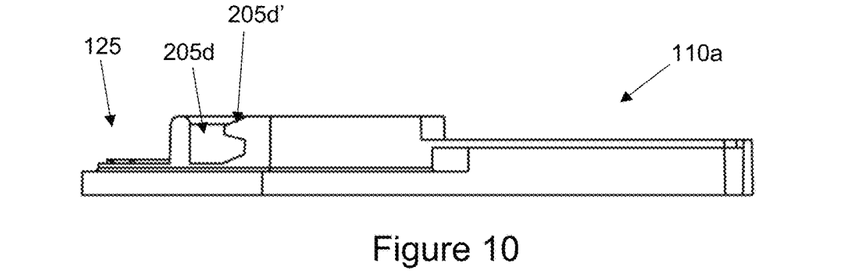
FIG. 10 illustrates a side view of the lower chassis of the lower tray assembly of FIG. 6.
Figure 11:
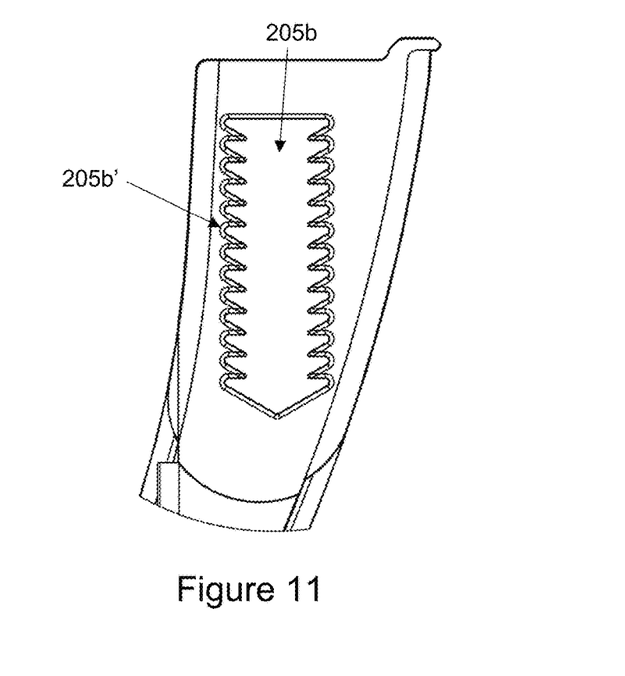
FIG. 11 illustrates an enlarged view of portion A of FIG. 8.

FIG. 6 illustrates a lower perspective view of the lower tray assembly 110, according to an embodiment of the present invention. FIG. 7 illustrates an upper perspective view of the lower chassis 110a, FIG. 8 illustrates a top view of the lower chassis 110a, FIG. 9 illustrates an end view of the lower chassis 110a, and FIG. 10 illustrates a side view of the lower chassis 110a. FIG. 11 illustrates an enlarged view of portion A of FIG. 8.

Figure 12:
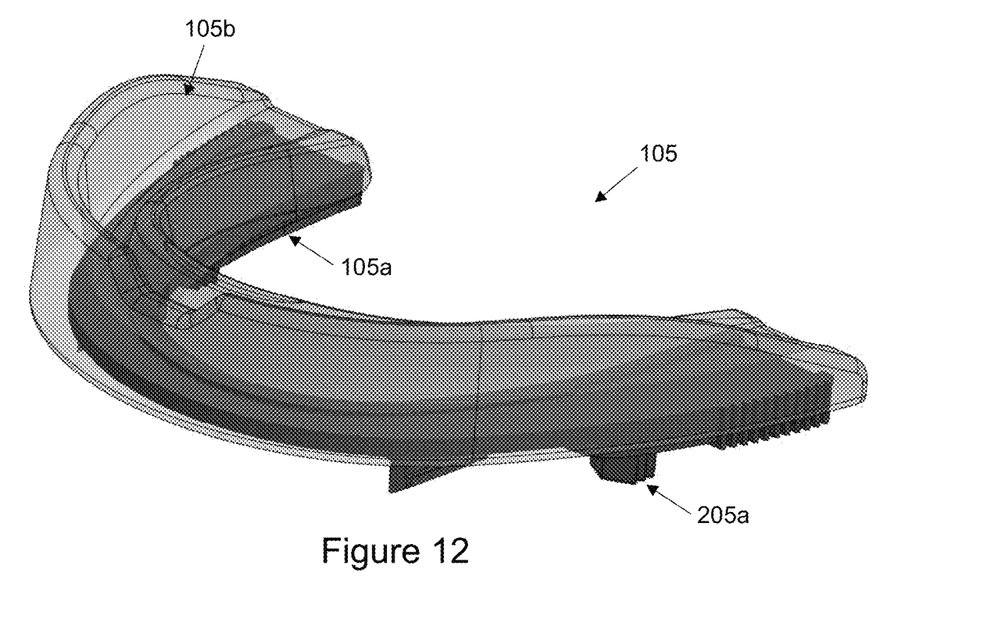
FIG. 12 illustrates an upper perspective view of an upper tray assembly of the device of FIG. 1, according to an embodiment of the present invention.
Figure 13:
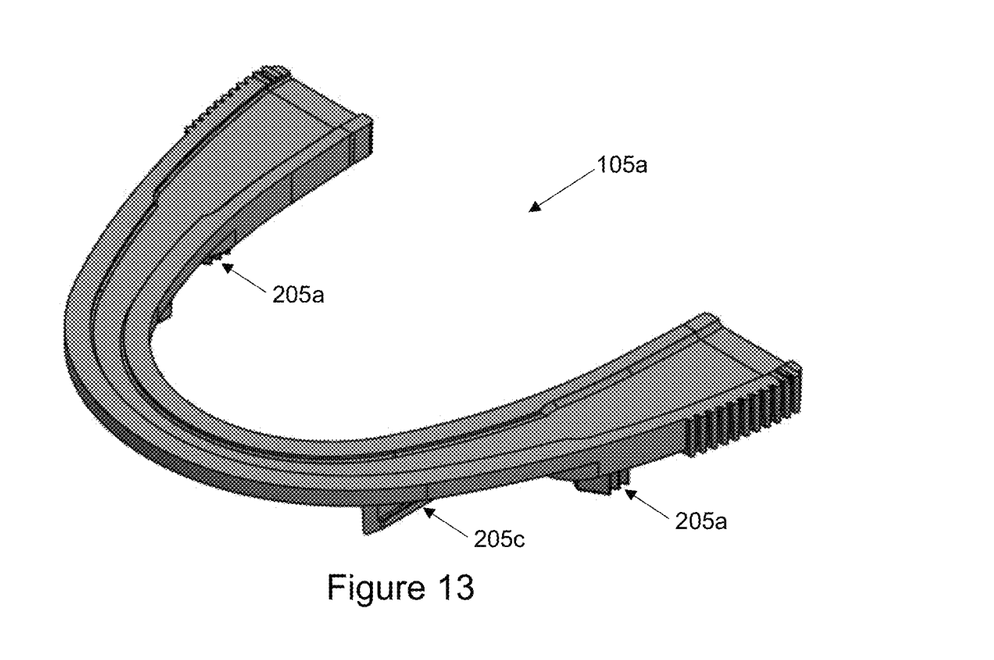
FIG. 13 illustrates an upper perspective view of an upper chassis of the upper tray assembly of FIG. 12.
Figure 14:
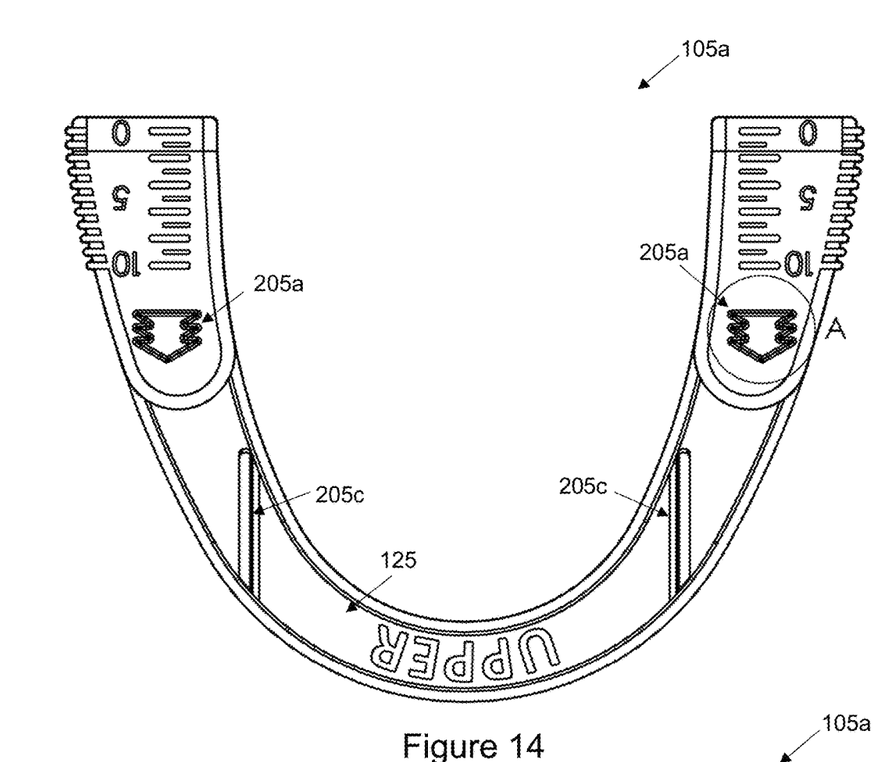
FIG. 14 illustrates a bottom view of the upper chassis of the upper tray assembly of FIG. 12.
Figure 15:
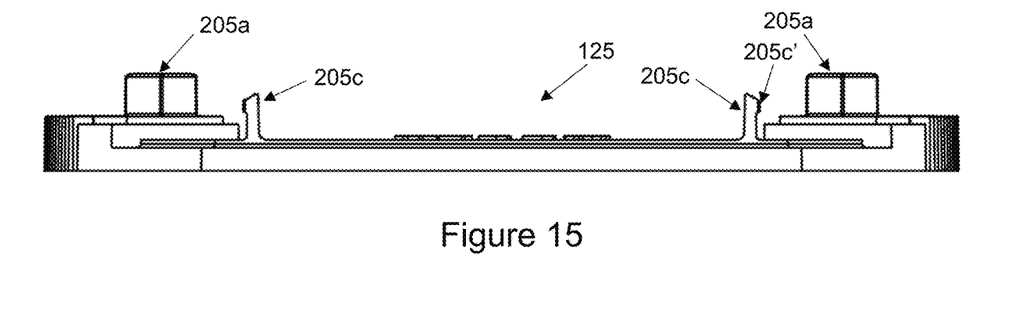
FIG. 15 illustrates an end view of the lower chassis of the upper tray assembly of FIG. 12.
Figure 16:
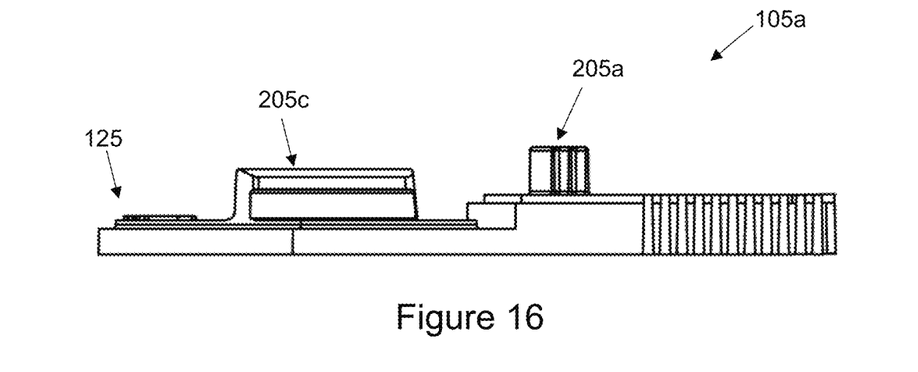
FIG. 16 illustrates a side view of the lower chassis of the upper tray assembly of FIG. 12.
Figure 17:
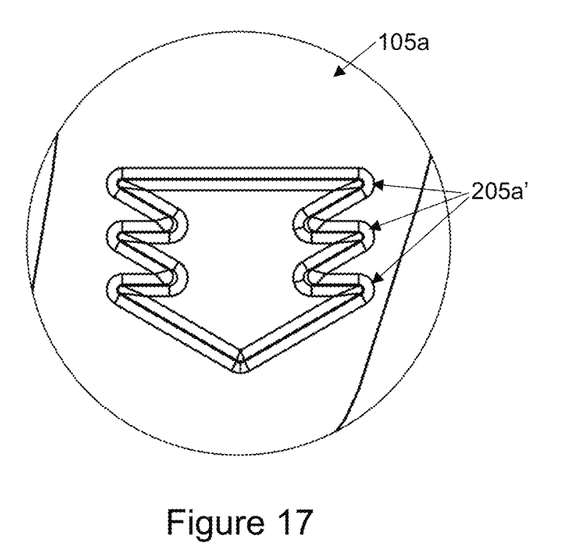
FIG. 17 illustrates an enlarged view of portion A of FIG. 14.

Similarly, FIG. 12 illustrates an upper perspective view of the upper tray assembly 110, according to an embodiment of the present invention. FIG. 13 illustrates an upper perspective view of the upper chassis 110a, FIG. 14 illustrates a bottom view of the upper chassis 110a, FIG. 15 illustrates an end view of the lower chassis 110a, and FIG. 16 illustrates a side view of the lower chassis 110a. FIG. 17 illustrates an enlarged view of portion A of FIG. 14.

The interlocking arrangement 205 includes locking members 205a in the upper chassis 105a and a partly corresponding locking recess (aperture) 205b in the lower chassis 110. The locking members and corresponding locking recess 205b are located in each of a pair of opposed posterior ends of the upper and lower chassis 105a, 110a and prevent relative translation of the upper and lower chassis in a transverse direction when the locking member 205a is in the locking recess 205b.

The locking member 205a is substantially uniform in cross section and extends downwardly (and outwardly) from a lower surface of the upper chassis 105a. The locking recess 205b is shaped to receive the locking member 205a in a plurality of predefined positions. The locking member 205 is pressed down into the locking recess 205b in one of these positions, and thus engages with the locking recess or aperture along the vertical axis.

In particular, the locking recess 205b includes a repeating locking pattern in the form of a sawtooth pattern comprising a plurality of cut outs 205b', and the locking member 205a includes a corresponding repeating locking pattern comprising a plurality of teeth 205a'. The teeth 205a' correspond with a subset of the cut outs 205b', and thus a portion of the locking recess 205b. As such, the locking member 205a may be placed in the locking recess 205b at a plurality of positions, i.e. wherein the teeth 205a' correspond to the cut outs 205b'.

As the locking recess 205b is elongate, and much longer than the locking member 205a, the locking recess 205b functions as a channel, wherein the locking member 205a is keyed to predefined positions along the length of the channel. However, in other embodiments, separate locking recesses may be provided for each of the locking members 205a and each of the predefined positions.

While the sawtooth arrangement has been illustrated, the skilled addressee will readily appreciate that any suitable locking pattern may be provided along the edges of the locking member 205a and locking recess 205b to prevent relative lateral movement of the upper and lower chassis 105a, 110a, and thereby "lock" the upper and lower tray assemblies 105, 110 to provide mandibular advancement. Similarly, while the locking pattern has been defined in a cross-sectional profile of the locking member 205a and locking recess 205b along their entire lengths, the skilled addressee will readily appreciate that the locking pattern may comprise protrusions or other formations that do not extend along the entire length of the locking member 205a or locking recess 205b.

Similarly, while the locking member 205a is defined in the upper chassis 105a and the recess 205b is defined in the lower chassis 110a, the skilled addressee will readily appreciate that such configuration may be reversed. Similarly, a combination of locking members 205a and recesses 205b may be provided in any configuration, including both upwardly and downwardly projecting locking members on a single device 100.

The interlocking arrangement 205 includes locking members 205a in the upper chassis 105a and a partly corresponding locking recess (aperture) 205b in the lower chassis 110. The locking members and corresponding locking recess 205b are located in each of a pair of opposed posterior ends of the upper and lower chassis 105a, 110a and prevent relative translation of the upper and lower chassis in a transverse direction when the locking member 205a is in the locking recess 205b.

The interlocking arrangement 205 further includes a guide members 205c in the upper chassis 105a and corresponding locking channels 205d in the lower chassis 110a. The guide members 205c and corresponding locking channels 205d are located on opposing sides of anterior ends of the upper and lower chassis 105a, 110a and prevent separation of the upper and lower chassis in a vertical direction when the guide member is in the locking channel.

As such, the locking members 205a and corresponding locking recess 205b, and the guide members 205c and corresponding locking channels 205d work together by preventing lateral and vertical movement, respectively.

The guide members 205c and the locking channels 205d engage with each other in a dovetail-like arrangement. In particular, the guide members 205c include an enlarged head 205c' which is received in the channel 205d and locked therein (in a vertical direction) by a retaining flange 205d'.

In use, the guide members 205c are placed into the locking channels 205d, and the upper and lower tray assemblies 105, 110 are slid to a desired offset. This may be achieved using the indicia 115, mentioned above. The locking members 205a are then pressed into their corresponding locking recess 205b, which prevents further lateral movement of the upper and lower tray assemblies 105, 110.

The different offsets define different levels of anterior protrusion of the lower tray relative to the upper tray along a posterior-anterior axis of the mandibular advancement device. In the device 100, ten (10) different offsets are provided by the predefined positions, approximately 1 mm apart. This is achieved by the size and shape of the teeth 205a' and cutouts 205b', namely three (3) teeth 205a' in the locking member 205a and thirteen (13) corresponding cutouts in the locking recess 205b.

The upper and lower chassis 105a, 110a include cut-outs 125 in the form of relatively thin portions which when joined define the opening 120. The thin material at the cut-outs 125 is located immediately adjacent to the trays 105b, 110b and thereby still provides rigidity to the device while providing an opening that is as large as possible.

The rigid upper chassis 105a and the rigid lower chassis 110a are unitarily formed, and may be moulded from any appropriately rigid material that is non-toxic and durable. Examples of such materials include Tritan Copolyesters from Eastman Chemical Company, Kingsport, Tenn., USA.

Similarly, the maxillary tray 105b and the mandibular tray 110b are unitarily formed by overmoulding over the rigid upper chassis 105a and the rigid lower chassis 110a respectively, and may be moulded from any appropriately comfortable material that is non-toxic and durable. Examples of such materials include ELVAX Copolymers from Dow Chemical Company, Midland, Mich., USA.

The maxillary tray 105b and the mandibular tray 110b are formed of another material than the rigid upper and lower chassis 105a 110a, to provide both comfort to the user (in soft trays 105b, 110b) with accuracy (from the rigid chassis 105a, 110a).

The use of thermoplastic material for the trays 105b, 110b enables the trays 105b, 110b to be heated (e.g. in hot or boiling water) and moulded to the user's mouth and teeth. This further provides comfort to a user, without requiring the trays to be custom made.

Furthermore, by overmoulding the trays 105b, 110b on the chassis 105a, 110b, the need for adhesives or fasteners between the trays 105b, 110b and chassis 105a, 110a is alleviated. As a result, the device 100 may be formed of only four unitarily formed components, which are joined to form simply two parts (the upper and lower tray assemblies 105, 110) which may be easily separated for cleaning.

Preferably, the device is BPA and latex free.

Advantageously, the devices described above provide a simple and cost effective way of mandibular advancement, which in turn may prevent or reduce snoring. The devices may help prevent the tongue of the user from collapsing into their throat. This may in turn reduce the risk of soft tissues coming close enough together to vibrate and cause a snoring sound. Furthermore, by keeping the airway free of obstruction, the user's body is able to get the proper oxygen levels it needs throughout the night to allow for a more restful night's sleep.

As the upper and lower tray assemblies completely detach and reattach in a simple manner, cleaning and adjustment of the device is simple. This enables the user to "micro-adjust" the advancement of the jaw in small increments (e.g. 10×1-millimetre increments). This ensures effectiveness by opening the airway sufficiently for the particular user, to help prevent their tongue from collapsing into their throat, without causing discomfort.

The device is particularly suitable for gradual advancement of the jaw, to enable the user to become used to having an advanced jaw, by enabling the user to make such adjustments themselves at home in a simple manner.

As the device uses soft trays overmoulded over a rigid chassis, a comfortable device is provided while accuracy is provided by the rigid chassis. In particular, the soft trays may cushion the teeth while sleeping. Furthermore, the use of thermoplastic enables the trays to be customised in a simple and cost effective manner.

Furthermore, as the upper and lower chassis engage with each other directly, the need for external members that may cause discomfort are avoided. In particular, there is no need for uncomfortable acrylics, screws, rubber bands, rods, or torsion members As there is a generous opening at the front of the device, users are able to breath through their mouth (or a combination of nose and mouth), which is particularly useful for mouth breathers. This may also reduce the likelihood of the user experiencing a claustrophobic feeling that some users get while wearing certain mouthpieces.

In the present specification and claims (if any), the word 'comprising' and its derivatives including 'comprises' and 'comprise' include each of the stated integers but does not exclude the inclusion of one or more further integers.

Reference throughout this specification to 'one embodiment' or 'an embodiment' means that a particular feature, structure, or characteristic described in connection with the embodiment is included in at least one embodiment of the present invention. Thus, the appearance of the phrases 'in one embodiment' or 'in an embodiment' in various places throughout this specification are not necessarily all referring to the same embodiment. Furthermore, the particular features, structures, or characteristics may be combined in any suitable manner in one or more combinations.

In compliance with the statute, the invention has been described in language more or less specific to structural or methodical features. It is to be understood that the invention is not limited to specific features shown or described since the means herein described comprises preferred forms of putting the invention into effect. The invention is, therefore, claimed in any of its forms or modifications within the proper scope of the appended claims (if any) appropriately interpreted by those skilled in the art.

What is claimed is:

1. A mandibular advancement device comprising:
   an upper tray assembly comprising a rigid upper chassis and a maxillary tray; and
   a lower tray assembly comprising a rigid lower chassis and a mandibular tray;
   wherein the rigid upper and rigid lower chassis define an interlocking arrangement configured to releasably lock the upper and lower tray assemblies into a selected one of a plurality of predefined positions, each of the predefined positions defining a different offset between the upper and lower tray assemblies to enable adjustment of a degree of mandibular advancement relative to a posterior-anterior axis when used; and
   wherein the interlocking arrangement includes locking channels and guide members on respective sides of an anterior portion of the mandibular advancement device, the locking channels and guide members each formed by the rigid lower chassis and the rigid upper chassis, respectively, the locking channels each extending along a length parallel to the posterior-anterior axis of the mandibular advancement device, the locking channels each being uniform in cross section normal to the posterior- anterior axis along the length, and the locking channels each including a laterally extending retaining flange, and the guide members of the rigid upper chassis configured to be received in the locking channels and retained by the laterally extending retaining flanges of the rigid lower chassis to prevent separation of the rigid upper and rigid lower chassis in a vertical direction, wherein the locking channels and guide members each extend from a labial edge to a lingual edge of the rigid lower chassis and the rigid upper chassis, respectively, and
   wherein the interlocking arrangement further includes a locking member and an at least partly corresponding locking recess or aperture in each posterior end of the mandibular advancement device to prevent relative movement in a transverse direction, wherein the locking members and the at least partly corresponding locking recesses or apertures are entirely posterior to the locking channels and guide members.

2. The mandibular advancement device of claim 1, wherein the different offsets define different levels of anterior protrusion of the mandibular tray relative to the maxillary tray.

3. The mandibular advancement device of claim 1, wherein at least 3 different offsets are provided by the plurality of predefined positions, and wherein the at least 3 different offsets include offsets between 0 mm and 10 mm.

4. The mandibular advancement device of claim 1, wherein the different offsets are provided at increments of 1 mm.

5. The mandibular advancement device of claim 1, wherein the mandibular advancement device includes indicia to identify a chosen offset.

6. The mandibular advancement device of claim 1, wherein each locking member is uniform in cross section, wherein each locking member extends outwardly from one of the upperand lower chassis, and each at least partly corresponding locking recess or aperture is defined in an opposite side of the rigid upper and rigid lower chassis.

7. The mandibular advancement device of claim 1, wherein each locking member is keyed to at least part of each at least partly corresponding locking recess or aperture.

8. The mandibular advancement device of claim 1, wherein each at least partly corresponding locking recess or aperture comprises an elongate locking channel, wherein each locking member is configured to be received in one of a plurality of predefined positions in the corresponding elongate locking channel.

9. The mandibular advancement device of claim 1, wherein each locking member includes a pattern along its edges corresponding to a portion of a repeating locking pattern.

10. The mandibular advancement device of claim 1, wherein the guide members and the locking channels engage with each other in a dovetail arrangement.

11. The mandibular advancement device of claim 1, wherein an opening is defined in the anterior portion of the mandibular advancement device to enable airflow therethrough when used.

12. The mandibular advancement device of claim 1, wherein the mandibular advancement device is U-shaped in plan view and is symmetrical around a sagittal plane.

13. The mandibular advancement device of claim 1, wherein the maxillary tray is formed of another material than the rigid upper chassis, wherein the maxillary tray is softer than the rigid upper chassis, and wherein the maxillary tray is overmoulded over the rigid upper chassis.

14. The mandibular advancement device of claim 1, wherein each of the rigid upper and rigid lower chassis is unitarily formed and each of the maxillary tray and mandibular tray is unitarily formed.

15. The mandibular advancement device of claim 1, wherein the maxillary tray and the mandibular tray are formed of a thermoplastic, enabling the maxillary and mandibular trays to be heated to be configured to form to a user's teeth and gums.

* * * * *